United States Patent [19]

Schneider

[11] Patent Number: 4,754,657
[45] Date of Patent: Jul. 5, 1988

[54] DISINTEGRATION TESTING DEVICE

[75] Inventor: Ortwin Schneider, Weiterstadt, Fed. Rep. of Germany

[73] Assignee: Erweka Apparatebau GmbH, Heusenstamm, Fed. Rep. of Germany

[21] Appl. No.: 17,164

[22] PCT Filed: Jun. 2, 1986

[86] PCT No.: PCT/EP86/00328
§ 371 Date: Dec. 11, 1986
§ 102(e) Date: Dec. 11, 1986

[87] PCT Pub. No.: WO86/07453
PCT Pub. Date: Dec. 18, 1986

[30] Foreign Application Priority Data

Jun. 4, 1985 [DE] Fed. Rep. of Germany ....... 3520034

[51] Int. Cl.⁴ ............................................. G01N 19/00
[52] U.S. Cl. ..................................................... 73/866
[58] Field of Search .................................. 73/866, 53

[56] References Cited

U.S. PATENT DOCUMENTS

| 3,618,395 | 11/1971 | Melliger | 73/866 |
| 3,742,190 | 6/1973 | Giani et al. | 73/866 X |
| 3,791,221 | 2/1974 | Kirschner et al. | 73/866 |
| 3,791,222 | 2/1974 | Goodhart et al. | 73/866 |
| 3,802,272 | 4/1974 | Bischoff et al. | 73/866 |
| 4,247,298 | 1/1981 | Rippie | 73/866 X |
| 4,279,860 | 7/1981 | Smolen | 73/866 X |
| 4,335,438 | 6/1982 | Smolen | 73/866 X |

FOREIGN PATENT DOCUMENTS 2409222 4/1975 Fed. Rep. of Germany.
2530065 3/1977 Fed. Rep. of Germany.
3246731 6/1984 Fed. Rep. of Germany.

Primary Examiner—Stewart J. Levy
Assistant Examiner—Joseph W. Roskos
Attorney, Agent, or Firm—Birch, Stewart, Kolasch & Birch

[57] ABSTRACT

A disintegration testing device for samples (20), in particular tablets, in which the samples (20) provided in a disintegration cage (10) inserted into a solvent, are positioned between a Hall generator (27) and a disk (21) having a magnet (28). When the sample (20) disintegrates the disk together with the magnet (28) approaches the Hall generator (27) so that the magnet (28) emits a signal which upon exceeding a switching threshold value is fed to a recording device and is displayed at display units (26). The disintegration cage (10) is removably arranged at the disintegration testing device and has no wired connections. The transmission of the energy for the electric circuitries in the disintegration cage (10) is provided by using contacts or by means of a high-frequency emitter and a high-frequency receiver. The transmission of the signals to the recording device is effected by means of opto-electronic components, in particular an infrared light bridge.

17 Claims, 3 Drawing Sheets

DISINTEGRATION TESTING DEVICE

The invention relates to a disintegration testing device for solid substance samples which disintegrate in a solvent, in particular tablets and the like, which includes a detachable disintegration cage which may be submerged into a solvent in a container, wherein the disintegration cage contains a sample held in position with a disk so that an electrical signal is generated when the sample is disintegrated.

A disintegration testing device already is known in which a water reservoir is provided for a housing, which reservoir is provided with a heating element for heating the water in the reservoir to a predetermined temperature. In the water bath several containers are filled with solvents, e.g. as a substitute for gastric juice. A disintegration cage which is formed out of a plurality of tubes each being closed at the bottom by a screen, is inserted into each container. A tablet is inserted into each tube as a sample and each is loaded with a disk of plastic material. In each tube electric lines are provided which are short circuited upon disintegration of the sample and in this manner the disintegration of the tablet is indicated. Electric lines are provided between the disintegration cages and the respective mounts for feeding the signals indicating the disintegration to an electronic recording device.

It appeared that the disintegration cages with the connecting cables are susceptible to failure and that the handling thereof is time-consuming. This is in particular true with regard to the cleaning of the disintegration cages and the charging of the cages with the sample.

The invention, therefore, is based on solving the problem of providing a disintegration testing device having a low susceptability of failure and being easy to handle.

According to the present invention these problems are solved in the disintegration testing device of the present invention as described hereinbelow.

The disintegration testing device according to the present invention has the advantage that it can be charged with samples in an easy manner since no electric lines protrude from the tubes of the disintegration cage. The disintegration cages can be cleaned in an easy manner since no wire connection exists between the disintegration cage and the actual disintegration testing device and/or the recording device, respectively.

Hall generators may be arranged laterally at the bottom part of the disintegration cage, e.g at each tube, and at respective positions a magnet may also be arranged laterally with respect to the disk. However, it appears to be advantageous to arrange the magnet at the bottom side of the disk and to arrange the Hall generator at a screen closing the disintegration cage at the bottom, preferably at the bottom side of the screen.

A particularly easy handling properly of the disintegration cage is realized when the energy and/or signals are transmitted in a wireless manner between a transmission unit fixed to a mount and the disintegration cage. The wireless transmission of signals is preferably effected using opto-electronic elements, preferably by means of an infrared light bridge. In this case the signals indicating the disintegration of a sample are first transmitted from the disintegration cage to the transmission unit and then are fed to the recording device. Furthermore, it turns out to be advantageous to transmit the energy for the power supply of the electric circuits arranged in the disintegration cage using a high-frequency emitter provided in the transmission unit and a high-frequency receiver arranged in the disintegration cage.

A particularly low-cost embodiment of the disintegration device, however, results when effecting the transmission of energy and/or signals between the transmission unit and the dissolution cage using electrical contacts. By the transmission of energy and signals in a wireless manner or by the use of electrical contacts it is guaranteed that no wire connection exists between the disintegration cage and the actual disintegration testing device so that the disintegration cage may be handled very easily.

The electric circuits which preferably are arranged in the top part of the disintegration cage, generate signals being suitable for a transmission to the recording device from the signals emitted from the Hall generator using a given switching threshold value.

The signals as well as the switching threshold values may be indicated on the disintegration cage by means of display elements, preferably by light emitting diodes. For recording the disintegration of the samples, e.g. the disintegration time, it is advantageous if the disintegration testing device comprises a recording unit which, e.g. is a computer.

In order to be able to use a disintegration cage quickly after a disintegration test as soon as possible it is advantageous if a heating station is provided with the disintegration testing device by means of which the disintegration cage can be dried very quickly. In a preferred embodiment the heating station comprises a radiator in order to avoid a direct contact of the Hall generators arranged at the bottom part of the disintegration cage and a heating plate.

A preferred embodiment of the disintegration testing device in accordance with the invention will now be explained in more detail while referring to the drawings. In the drawings.

Figures 1, 2:
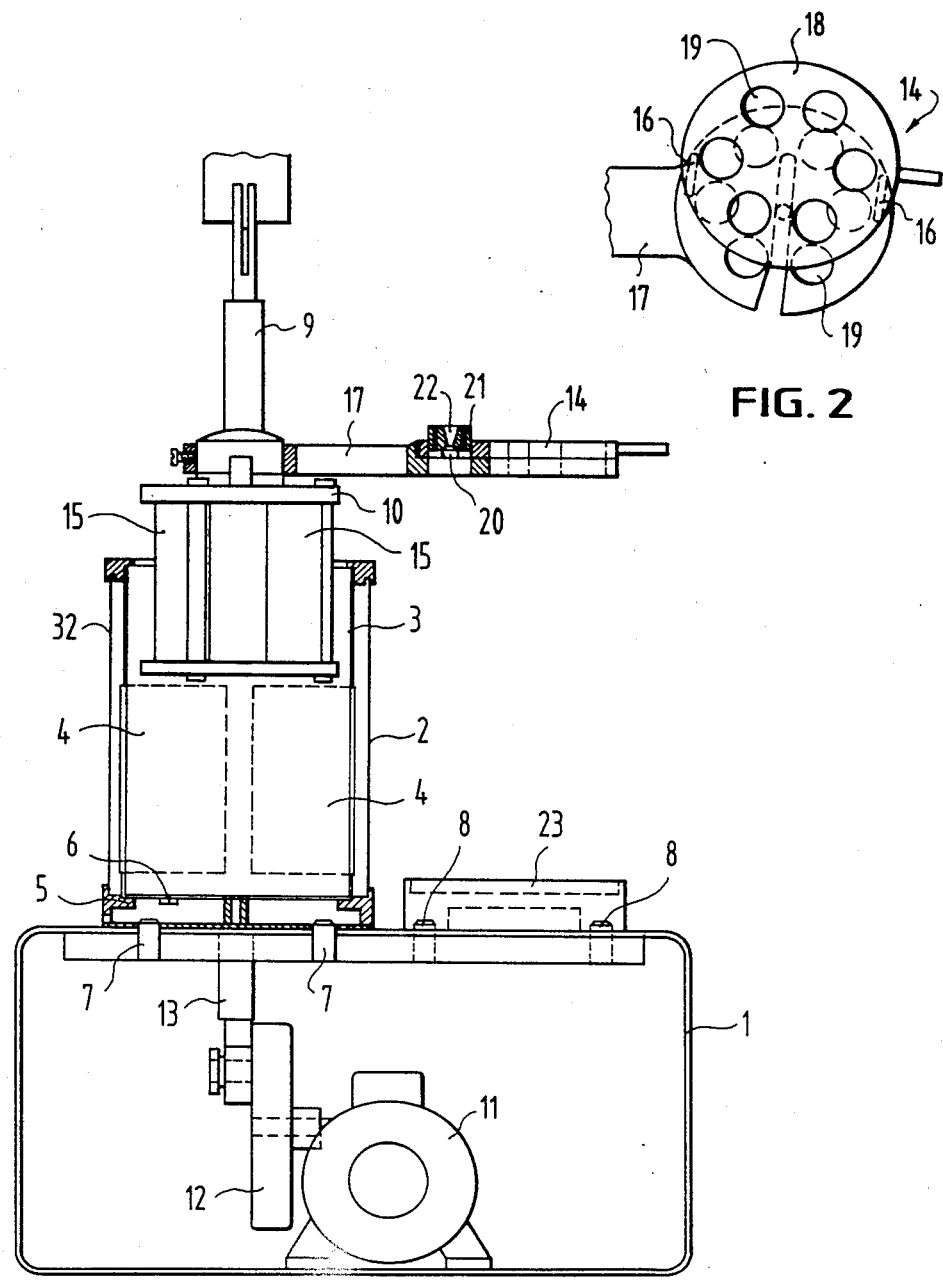
FIG. 1 is a front view of the disintegration testing device.
FIG. 2 is a charging means.

In the disintegration testing device shown in FIG. 1, a container 2 with a solvent, in particular a substitute for gastric juice, is detachably arranged at the bottom part of a housing 1. The container 2 is heated to a constant temperature of, e.g. 37° C., by means of a heating means comprising heating members 4 and a heating control means arranged in the bottom part 5 of the container 2 and comprising a thermostat 6. The electrical connection between the housing 1 and the container 2 is effected by contacts 7 being arranged at the housing 1 and at the bottom part 5 of the container 2. For example, three contacts 7 are provided, two of which contacts are used for voltage supply of 24 V for the heating means as well as for the heating control means, the remaining contact 7 serving for a display being correlated to the thermostat 6. The contacts preferably have the form of pins disposed in the housing which pins protrude through bores of the bottom part 5 of the container 2 and there cooperate with corresponding contacts.

To the side of the station for the container 2 a further station with further contacts 8 is provided for a further container 2, e.g. for preheating said further container 2 prior to the disintegration testing.

Behind the container 2 a support member 9 for a disintegration cage 10 is shown in part. Upon having been charged with samples, e.g. tablets, the disintegration cage 10 is submerged into the solvent, and the time is measured until the sample disintegrated. The solvent is in a beaker 3, which e.g. is made of V2A-steel, and a protecting tube 32, which e.g. is made of V2A-steel, is provided around the beaker. The disintegration cage 10 is continuously moved in upward and downward directions during the disintegration tests using a motor 11, an eccentric 12 and a lifting rod 13.

For simultaneously charging the disintegration cage 10 with samples, a system 14 is provided which is shown in detail in FIG. 2.

The disintegration cage 10 has a plurality of parallel tubes 15 being open on the top and being closed by means of a screen to the bottom. For simultaneously charging the plurality of tubes 15, a part 18 being slidably connected to a stationary part 17 by means of elongated openings 16 and relating pins, is shifted such that bores 19 in both parts 17 and 18 do not correspond with each other. Thereafter, one sample 20 and one disk 21, preferably of a plastic material and being provided with a nozzle-like opening 22, are inserted into each of the bores 19 of the part 18. Upon having shifted part 18 over part 17 in such manner that the bores 19 correspond with each other, all the samples 20 and disks 21 simultaneously fall into the tubes 15. After this the charging system 14 is moved out of its operating position over the disintegration cage.

On the side of the support member 9 and behind the station with the further contacts 8, a heating station 23 is additionally arranged on the housing 1 for drying the disintegration cages 10 after the disintegration test.

Figures 3, 4:
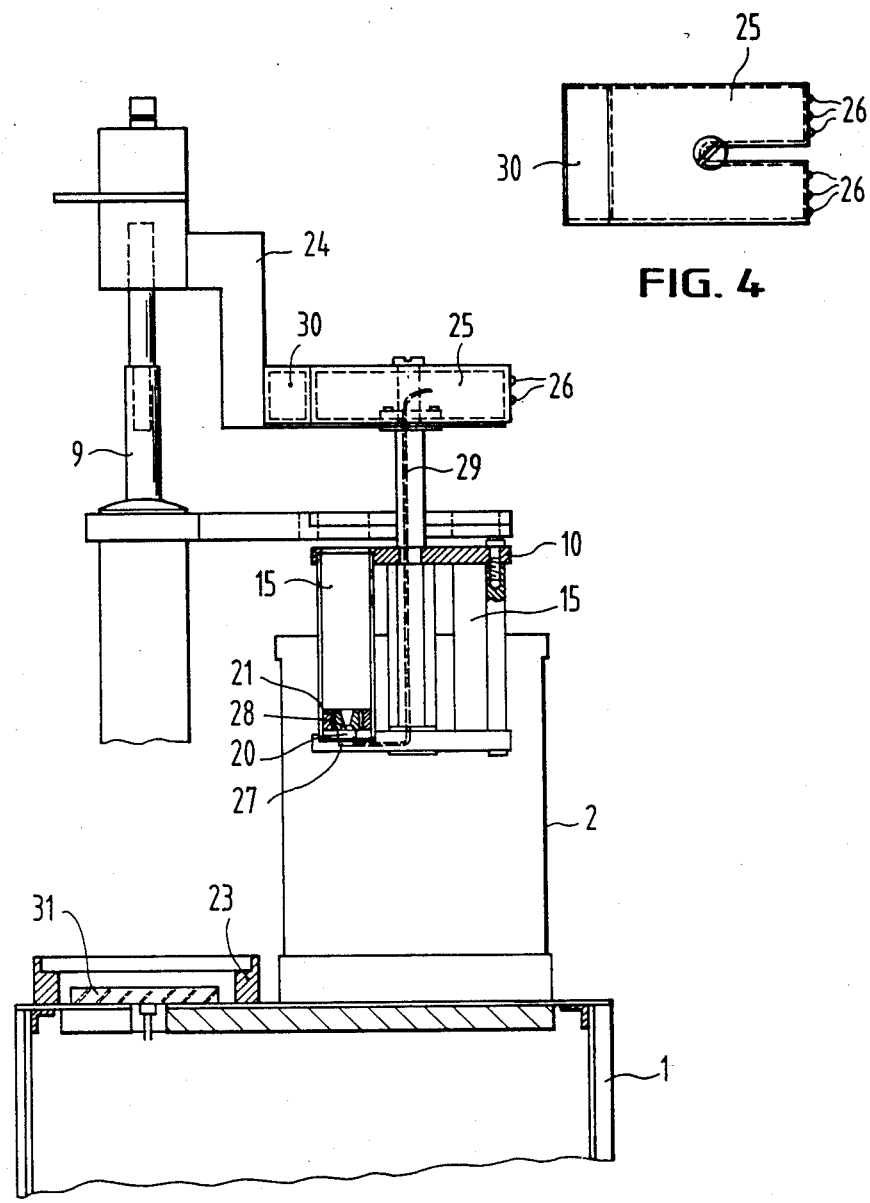
FIG. 3 is a side view of the disintegration testing device.
FIG. 4 is a top view of the top part of the disintegration cage.

FIG. 3 shows the outlines of the container 2 into which the disintegration cage 10 is inserted. The dissolution cage 10 is removably arranged at a mount 24 of the support member 9 by means of a upper head part 25. The head part 25 contains electric circuits and display units 26 for indication of the point in time when a sample 20 has disintegrated.

The point in time of disintegration is determined by a Hall generator 27 emitting an electric signal when a magnet 28 arranged at the bottom side of the disk 21, comes into the proximity of the generator upon disintegration of the sample 20. A connecting cable 29 feeds the signal to the electric circuits in the head part 25. The Hall generator as well as the cable are arranged under a protective cover.

The head part 25 is shown in top view in FIG. 4. As the disintegration cage 10 is removable, it is provided with energy for powering the electric circuits through the support member 9 and the mount 24 by means of a transmission unit 30 through contacts being arranged between the transmission unit 30 and the head part 25 or through a high-frequency emitter arranged in the transmission unit 30 and a high-frequency receiver arranged in the head part 25. Correspondingly, signals between the transmission unit 30 and the head part 25 may be transmitted through electric contacts or also through optoelectronic components, e.g. through an infrared light bridge. These signals may be signals indicating the disintegration of the sample which signals on the one hand are displayed at the display elements 26 and on the other hand are transmitted to a recording unit which preferably is built as a computer. The signals are generated upon exceeding a given switching threshold value which also may be indicated by means of the display elements 26.

After the disintegration test, the dissolution cage 10 is removed out of the solvent, washed out and dried at the heating station 23 arranged behind the support member 9, which station comprises a radiator 31 which dries the disintegration cage 10 without touching it.

Figure 5:
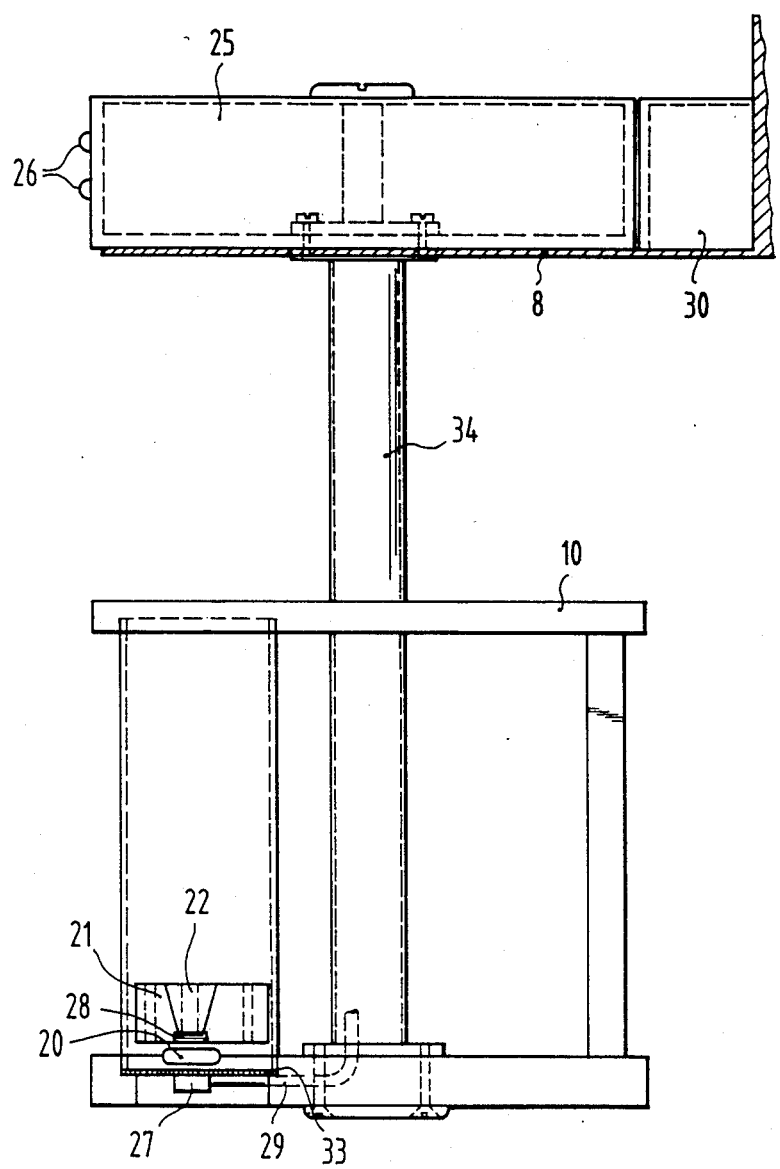
FIG. 5 is an enlarged view of the disintegration cage.

In the enlarged view in FIG. 5 of the disintegration cage only one tube 15 is shown which tube is closed at its bottom end by a screen 33. At the bottom side of the screen the Hall generator 27 is arranged in protected position. Between the screen 33 and the disk 21 the sample 20 is arranged around which a flow of solvent is provided through the nozzle-like opening 22 in the disk 21 when the disintegration cage 10 is submerged and moved backwards and forwards by means of the motor 11. The magnet 28 is arranged at the bottom side of the disk 21 at a position related to the Hall generator 27. Upon disintegration of the sample 20 the magnet 28 together with the disk 21 is moved in the direction of the Hall generator 27 so that the Hall generator generates a respective signal which, after exceeding the switching threshold, is transferred in the electric circuitry into a signal indicating the disintegration of the sample 20, which latter signal on the one hand is transmitted via the contacts or the infrared light bridge to the recording device and on the other hand is displayed by the display units 26. The connecting cable 29 between the Hall generator 27 and the electric circuits in the head part 25 is passed through a tube 34. The Hall generator also may be arranged on the side of the tube 15 if the magnet 28 also is arranged at a corresponding position on the side of the disk 21. Also in this case a respective signal is generated by moving the magnet 28 past the Hall generator 27 when the sample 20 disintegrates.

I claim:

1. A disintegration testing device for testing the disintegration of samples of solid material that disintegrate in a solvent which comprises:

a support structure including a mount member;

a container supported by said support structure for containing solvent;

a disintegration cage supported by said mount member for being submerged into said solvent contained in said container, wherein said disintegration cage includes at least one Hall generator disposed at a lower part of said disintegration cage, and at least one disk corresponding to said Hall generator and disposed above said Hall generator in said disintegration cage for positioning a sample between said disk and said Hall generator, said disk containing a magnet; and moving means operatively connected to said support structure and said disintegration cage for moving said disintegration cage when it is submerged in said solvent so as to cause said solvent to circumcirculate and flow about said sample;

wherein upon disintegration of said sample in said solvent contained in said container, said magnet approaches said Hall generator which generates an electrical signal indicating the disintegration of said sample.

2. A dissolution testing device according to claim 1, wherein said magnet is disposed at the bottom side of said disk, and a screen for supporting said sample is disposed in said dissolution cage between said Hall generator and said disk.

3. A disintegration testing device according to claim 1, further comprising a transmission unit disposed on said mount member for supplying energy to said disintegration cage and for receiving signals from said disintegration cage indicating the disintegration of said sample, and a wireless means operatively associated with said transmission unit and said disintegration cage for effecting the transmission of energy and signals between said transmission unit and said disintegration cage.

4. A disintegration testing device according to claim 3, wherein said wireless means comprises opto-electronic components.

5. A disintegration testing device according to claim 3, wherein said wireless means comprises a high-frequency emitter operatively disposed in said transmission unit and a high-frequency receiver operatively disposed in said disintegration cage.

6. A disintegration testing device according to claim 3, wherein said wireless means comprises electrical contacts.

7. A disintegration testing device according to claim 1, wherein said disintegration cage includes electric circuit means operatively associated therewith for generating a signal indicating the disintegration of said sample from signals generated by said Hall generators based on a predetermined switching threshold value.

8. A disintegration testing device according to claim 7, wherein said disintegration cage includes display units operatively connected thereto for displaying information indicating the disintegration of said sample and said switching threshold values.

9. A disintegration testing device according to claim 8, wherein said display units comprise light emitting diodes.

10. A disintegration testing device according to claim 9, further comprising a recording device operatively connected to said disintegration testing device for measuring the disintegration time of said sample.

11. A disintegration testing device according to claim 10, further comprising a heating station operatively associated with said disintegration testing device for supporting and drying said disintegration cage upon removal of said solvent.

12. A disintegration testing device according to claim 11, wherein said heating station comprises a radiator.

13. A disintegration testing device according to claim 6, wherein said heating station comprises a radiator, said disintegration testing device further comprising a sample charging system operatively connected to said support structure for charging said disintegration cage with at least one sample, wherein said sample charging system includes a stationary member having first sample holes formed therein and a slidable member having second sample holes formed therein corresponding to said first sample holes, said slidable member being slidably mounted on said stationary member, and wherein said second sample holes only align with said first sample holes when said slidable member is moved to a charging position so as to allow said disk and said sample to drop into said disintegration cage, said disk and said sample being prevented from dropping into said disintegration cage when said sample holes are not aligned.

14. A disintegration testing device according to claim 13, wherein said disk includes a nozzle opening disposed above said magnet for providing an effective flow of solvent around said sample, and wherein said moving means comprises a lifting rod operatively connected to said disintegration cage in upward and downward directions, an eccentric member operatively connected to said lifting rod for moving said lifting rod, and a motor operatively connected to said eccentric member for moving said eccentric member.

15. A disintegration testing device according to claim 1, which further comprises a sample charging system operatively connected to said support structure for charging said disintegration cage with at least one sample, wherein said sample charging system includes a stationary member having first sample holes formed therein and a slidable member having second sample holes formed therein corresponding to said first sample holes, said slidable member being slidably mounted on said stationary member, and wherein said second sample holes only align with said first sample holes when said slidable member is moved to a charging position so as to allow said disk and said sample to drop into said disintegration cage, said disk and said sample being prevented from dropping into said disintegration cage when said sample holes are not aligned.

16. A disintegration testing device according to claim 1, wherein said disk includes a nozzle opening disposed above said magnet for providing an effective flow of solvent around said sample.

17. A disintegration testing device according to claim 1, wherein said moving means comprises a lifting rod operatively connected to said disintegration cage for moving said disintegration cage in upward and downward directions, an eccentric member operatively connected to said lifting rod for moving said lifting rod, and a motor operatively connected to said eccentric member for moving said eccentric member.

* * * * *